US011065118B2

(12) United States Patent
Keren et al.

(10) Patent No.: US 11,065,118 B2
(45) Date of Patent: Jul. 20, 2021

(54) CARDIAC VALVE COMMISSURE BRACE

(71) Applicant: The Medical Research, Infrastructure and Health Services Fund Of The Tel-Aviv Medical Center, Tel Aviv (IL)

(72) Inventors: Gad Keren, Kiryat Ono (IL); Allan C. Entis, Tel Aviv (IL)

(73) Assignee: The Medical Research, Infrastructure And Health Services Fund Of the Tel-Aviv Medical Center, Tel Aviv (IL)

(*) Notice: Subject to any disclaimer, the term of this patent is extended or adjusted under 35 U.S.C. 154(b) by 0 days.

(21) Appl. No.: 14/772,394

(22) PCT Filed: Mar. 4, 2014

(86) PCT No.: PCT/IB2014/059435
§ 371 (c)(1),
(2) Date: Sep. 3, 2015

(87) PCT Pub. No.: WO2014/136056
PCT Pub. Date: Sep. 12, 2014

(65) Prior Publication Data
US 2016/0045314 A1 Feb. 18, 2016

Related U.S. Application Data

(60) Provisional application No. 61/772,212, filed on Mar. 4, 2013.

(51) Int. Cl.
*A61F 2/24* (2006.01)
(52) U.S. Cl.
CPC .......... *A61F 2/2454* (2013.01); *A61F 2/2442* (2013.01); *A61F 2/2445* (2013.01);
(Continued)

(58) Field of Classification Search
CPC ...................................................... A61F 2/2442
See application file for complete search history.

(56) References Cited

U.S. PATENT DOCUMENTS 2,748,766 A * 6/1956 Coates ................ A61F 13/0203
602/58
3,036,572 A * 5/1962 Castelli ................ A61F 15/006
24/380
(Continued)

FOREIGN PATENT DOCUMENTS

WO 0044311 8/2000
WO 2011047168 4/2011

OTHER PUBLICATIONS

International Search Report; dated Jul. 9, 2014, Application No. PCT/IB2014/059435, Filed on Mar. 4, 2014.

*Primary Examiner* — Jacqueline Woznicki
(74) *Attorney, Agent, or Firm* — A.C. Entis-IP Ltd.; Allan C. Entis (57) ABSTRACT

A brace for mounting to an annulus of a cardiac valve, the brace comprising: first and second bottom gripping wings for gripping the annulus; first and second top gripping wings for gripping the annulus; and a support bridge that connects the top wings to the bottom wings; wherein the brace is deformable from a delivery configuration to a deployed configuration and in the delivery configuration the top wings are oriented substantially back to back along an axis and the bottom wings are oriented substantially back to back along the same axis, and in the deployed configuration the first top and bottom gripping wings face each other to grip the annulus between them and the second top and bottom gripping wings face each other to grip the annulus between them.

12 Claims, 10 Drawing Sheets

(52) U.S. Cl.
CPC .... *A61F 2/2451* (2013.01); *A61F 2210/0014* (2013.01); *A61F 2220/0016* (2013.01); *A61F 2230/0013* (2013.01); *A61F 2230/0039* (2013.01)

(56) References Cited

U.S. PATENT DOCUMENTS

| | | | | |
|---|---|---|---|---|
| 5,180,381 | A * | 1/1993 | Aust | A61B 17/7059 606/280 |
| 5,360,444 | A * | 11/1994 | Kusuhara | A61F 2/2445 623/2.36 |
| 5,569,250 | A * | 10/1996 | Sarver | A61B 17/688 606/281 |
| 5,733,249 | A * | 3/1998 | Katzin | A61F 5/0106 602/21 |
| 5,792,155 | A * | 8/1998 | Van Cleef | A61B 17/12022 606/158 |
| 5,843,018 | A * | 12/1998 | Shesol | A61F 13/02 602/79 |
| 6,458,153 | B1 * | 10/2002 | Bailey | A61F 2/2418 623/1.24 |
| 6,719,767 | B1 | 4/2004 | Kimblad | |
| 6,723,038 | B1 * | 4/2004 | Schroeder | A61B 17/00234 600/16 |
| 6,752,813 | B2 * | 6/2004 | Goldfarb | A61B 50/30 606/139 |
| 6,913,608 | B2 * | 7/2005 | Liddicoat | A61B 17/00234 606/151 |
| 7,363,926 | B2 * | 4/2008 | Pflueger | A61F 2/203 128/200.24 |
| 8,333,777 | B2 * | 12/2012 | Schaller | A61B 17/00234 606/139 |
| 8,382,829 | B1 * | 2/2013 | Call | A61B 17/0401 623/2.37 |
| 8,480,707 | B2 * | 7/2013 | Pavcnik | A61B 17/0057 606/151 |
| 8,551,143 | B2 * | 10/2013 | Norris | A61B 17/8061 606/280 |
| 2003/0083742 | A1 * | 5/2003 | Spence | A61F 2/2412 623/2.16 |
| 2003/0120340 | A1 * | 6/2003 | Liska | A61F 2/2454 623/2.1 |
| 2003/0233022 | A1 * | 12/2003 | Vidlund | A61B 17/00234 600/16 |
| 2004/0049211 | A1 * | 3/2004 | Tremulis | A61B 17/0401 606/153 |
| 2004/0127981 | A1 * | 7/2004 | Rahdert | A61F 2/2454 623/2.36 |
| 2004/0127982 | A1 * | 7/2004 | Machold | A61F 2/2418 623/2.36 |
| 2004/0138745 | A1 * | 7/2004 | Macoviak | A61F 2/2412 623/2.36 |
| 2004/0260317 | A1 * | 12/2004 | Bloom | A61F 2/2487 606/151 |
| 2005/0070999 | A1 * | 3/2005 | Spence | A61F 2/2418 623/2.37 |
| 2005/0143811 | A1 * | 6/2005 | Realyvasquez | A61F 2/2445 623/2.36 |
| 2006/0020336 | A1 * | 1/2006 | Liddicoat | A61B 17/0644 623/2.37 |
| 2006/0195183 | A1 * | 8/2006 | Navia | A61F 2/2409 623/2.18 |
| 2006/0206047 | A1 * | 9/2006 | Lampe | A61F 13/04 602/42 |
| 2009/0264995 | A1 * | 10/2009 | Subramanian | A61F 2/2454 623/2.36 |
| 2010/0100108 | A1 | 4/2010 | Goldfarb et al. | |
| 2010/0121435 | A1 * | 5/2010 | Subramanian | A61F 2/2445 623/2.11 |
| 2010/0121437 | A1 * | 5/2010 | Subramanian | A61F 2/2445 623/2.36 |
| 2010/0131057 | A1 * | 5/2010 | Subramanian | A61F 2/2445 623/2.36 |
| 2012/0059458 | A1 | 3/2012 | Buchbinder et al. | |
| 2016/0128873 | A1 * | 5/2016 | Martin | A61F 13/00042 604/360 |
| 2016/0310254 | A1 * | 10/2016 | Ferrand | B65D 11/14 |
| 2017/0189186 | A1 * | 7/2017 | Mohl | A61F 2/2454 |
| 2018/0125494 | A1 * | 5/2018 | Hall | A61B 17/11 |
| 2018/0185197 | A1 * | 7/2018 | Detwiler | A61F 13/105 |
| 2018/0214270 | A1 * | 8/2018 | Subramanian | A61B 17/00 |

* cited by examiner

CARDIAC VALVE COMMISSURE BRACE

RELATED APPLICATIONS

The present application is a US National Phase of PCT Application No. PCT/IB2014/059435, filed on Mar. 4, 2014 claiming benefit under 35 U.S.C. 119(e) of U.S. Provisional Application 61/772,212 filed on Mar. 4, 2013, the disclosures of which are incorporated herein by reference.

TECHNICAL FIELD

Embodiments of the invention relate to devices and instruments for implementing cardiac valve corrective surgery.

BACKGROUND

The human heart, and generally all mammalian hearts, comprises two blood pumps that operate in synchrony to oxygenate and deliver oxygenated blood to the body. A first pump receives deoxygenated blood after it has coursed through blood vessels in the circulatory system to deliver oxygen and nutrients to the various parts the body, and pumps the deoxygenated blood through the lungs to be oxygenated. The second pump receives the oxygenated blood from the lungs and pumps it to flow through the blood vessels of the circulatory system and deliver oxygen and nutrients to the body parts. The two pumps are located adjacent each other in the heart and each pump comprises two chambers, an atrium that receives blood and a ventricle that pumps blood.

The first pump, which receives deoxygenated blood to be pumped to the lungs, is located on the right side of the heart and its atrium and ventricle are accordingly referred to as the right atrium and right ventricle. The second pump, which receives oxygenated blood to be pumped to the body, is located on the left side of the heart and its atrium and ventricle are referred to as the right atrium and right ventricle of the heart. The right and left atria are separated by a wall in the heart referred to as the interatrial septum and the right and left ventricles are separated by a wall in the heart referred to as the interventricular septum.

Deoxygenated blood enters the right atrium via blood vessels referred to as the superior vena cava and inferior vena cava. During a part of the heart cycle referred to as diastole the right ventricle is relaxed and the deoxygenated blood in the right atrium flows from the right atrium into the right ventricle via a valve, referred to as a tricuspid valve, which connects the right atrium to the right ventricle. The right ventricle contracts during a part of the heart cycle referred to as systole, to pump the deoxygenated blood that it receives from the right atrium out of the ventricle and into the pulmonary artery via a valve referred to as the pulmonary valve, which interfaces the pulmonary artery with the right ventricle. The pulmonary artery delivers the deoxygenated blood to the lungs for oxygenation. The tricuspid and pulmonary valves control direction of blood flow in the right side of the heart. The tricuspid valve opens to let deoxygenated blood flow from the right atrium into the right ventricle and closes to prevent deoxygenated blood from regurgitating into the right atrium when the right ventricle contracts. The pulmonary valve opens to let blood enter the pulmonary artery when the right ventricle contracts and closes to prevent blood regurgitating into the right ventricle when the right ventricle relaxes to receive blood from the right atrium.

The left atrium receives oxygenated blood from the lungs via pulmonary veins. Oxygenated blood flows from the left atrium into the left ventricle during diastole via a bileaflet valve referred to as the mitral valve, which opens during diastole to allow blood flow from the left atrium to the left ventricle. The left ventricle contracts during systole to pump the oxygenated blood that it receives from the left atrium out of the heart through the aortic valve and into the aorta, for delivery to the body. The mitral valve operates to prevent regurgitation of oxygenated blood from the left ventricle to the left atrium when the left ventricle contracts to pump oxygenated blood into the aorta. The aortic valve closes to prevent blood from regurgitating into the left ventricle when the left ventricle relaxes to receive blood from the left atrium.

Each valve comprises a set of matching "flaps", also referred to as "leaflets" or "cusps". that are mounted to and extend from a supporting structure of fibrous tissue. The supporting structure has a shape reminiscent of an annulus and is often conventionally referred to as the annulus of the valve. The leaflets are configured to align and overlap each other, or coapt, along free edges of the leaflets to close the valve. The valve opens when the leaflets are pushed away from each other and their free edges part. The aortic, pulmonary, and tricuspid valves comprise three leaflets. The mitral valve comprises two leaflets.

The leaflets in a valve open and close in response to a gradient in blood pressure across the valve generated by a difference between blood pressure on opposite sides of the valve. When the gradient is negative in a "downstream flow" or antegrade direction, in which direction the valve is intended to enable blood flow, the leaflets are pushed apart in the downstream, antegrade direction by the pressure gradient, and the valve opens. When the gradient is positive in the downstream direction, the leaflets are pushed together in the upstream or retrograde direction so that their respective edges meet to align and coapt, and the valve closes.

For example, the leaflets in the mitral valve are pushed apart during diastole to open the mitral valve and allow blood flow from the left atrium into the left ventricle when pressure in the left atrium is greater than pressure in the left ventricle. The leaflets in the mitral valve are pushed together so that their edges coapt to close the valve during systole when pressure in the left ventricle is greater than pressure in the left atrium to prevent regurgitation of blood into the left atrium.

Each valve is configured to prevent misalignment or prolapse of its leaflets as a result of positive pressure gradients pushing the leaflets upstream past a region in which the leaflets properly align and coapt to close the valve. A construction of fibrous tissue in the leaflets of the pulmonary and aortic valves operates to prevent prolapse of the leaflets in the pulmonary and aortic valves. A configuration of cord-like tendons, referred to as chordae tendineae, connected to muscular protrusions, referred to as papillary muscles, that project from the left ventricle wall, tie the leaflets of the mitral valve to the walls of the left ventricle. The chordae tendineae provide dynamic anchoring of the mitral valve leaflets to the left ventricle wall that operate to limit upstream motion of the leaflets and prevent their prolapse into the left atrium during systole. Similarly, a configuration of chordae tendineae and papillary muscles cooperate to prevent prolapse of the tricuspid valve leaflets into the right atrium.

Efficient cardiac valve function can be complex and a cardiac valve may become compromised by disease or injury to an extent that warrants surgical intervention to effect its repair or replacement. For example, normal mitral valve opening and closing and prevention of regurgitation of blood from the left ventricle into the left atrium is dependent on coordinated temporal cooperation of the mitral leaflets, the mitral annulus, the chordae, papillary muscles, left ventricle, and left atrium. Malfunction of any of these components of a person's heart may lead to mitral valve dysfunction and regurgitation that warrants surgical intervention to provide the person with an acceptable state of health and quality of life.

SUMMARY

An aspect of an embodiment of the invention relates to providing a structure and procedures for emplacing and securing the structure to an annulus of a cardiac valve that may operate to improve functioning of the valve, and/or provide structural support for apparatus that operates to improve functioning of the valve. According to an aspect of an embodiment of the invention, the structure, hereinafter also referred to as an "annular brace" or a "brace", is configured to grip and anchor to an annulus of a cardiac valve in a region of a commissure of the valve.

In an embodiment of the invention, the annular brace comprises first and second bottom gripping wings and first and second top gripping wings for gripping and anchoring to the annulus of the cardiac valve in a region of the commissure. The top gripping wings are connected to the bottom gripping wings by a support bridge. The annular brace has a delivery configuration and a deployed configuration, and is formed from a suitable deformable biocompatible material so that the brace is deformable from the delivery configuration to the deployed configuration. Optionally, the deformable biocompatible material is a shape memory alloy such as nitinol. In the delivery configuration the shape memory alloy brace may be in a martensite state and in the deployed configuration the material may be in an austenite state.

In the delivery configuration the first and second bottom gripping wings are folded to lie substantially back to back along a same axis and the first and second top gripping wings are folded to lie substantially back to back along the same axis along which the bottom gripping wings lie. In the deployed configuration, the first top and first bottom gripping wings oppose each other to grip a first region of the annulus between them, and the second top and second bottom gripping wings oppose each other to grip a second region of the annulus between them. The gripping wings are shaped to conform to the curvature of the annular regions that they grip. The first and second regions of the annulus lie on opposite sides of the commissure.

A deployment catheter houses the brace in the delivery configuration for delivery to and for positioning the brace for deployment at the cardiac valve. Following delivery and positioning at the commissure, the deployment catheter is controlled to release the annular brace so that the brace may deform to the deployed state and grip and anchor to the annulus.

In an embodiment of the invention, the top and bottom first gripping wings are integral portions of a same first "gripping strip" of an elastically deformable biocompatible material and the top and bottom second gripping wings are integral portions of a second gripping strip of an elastically deformable biocompatible material. A bridge portion of the first gripping strip located between the first gripping strip's top and bottom wings is connected to a bridge portion of the second gripping strip located between the second gripping strip's top and bottom gripping wings to form the bridge connecting both top wings to both bottom wings.

In the delivery configuration of the annular brace, the strips are flat and lie substantially back to back. In the deployed configuration the strips are bent so that the top and bottom wings of the first strip face each other to grip the first region of the annulus and the top and bottom wings of the second strip face each other to grip the second region of the annulus. The deployment catheter that houses the brace for delivery to the annulus optionally constrains the brace to the brace's delivery configuration. Upon release from the deployment catheter, the brace, optionally, self deforms to the brace's deployed configuration.

In an embodiment of the invention the first and second gripping strips are separate strips and their respective bridge portions are connected using any of various suitable joining process, such as bonding, gluing, welding, or brazing. Optionally, the first and second gripping strips and the bridge are integral parts of a same piece, hereinafter also referred to as a "die-shape", of material shaped by a process such as by way of example, stamping or laser cutting from a sheet of an elastically deformable biocompatible material. Suitably bending the die-shape deforms the die-shape to the delivery configuration of the brace.

In an embodiment of the invention, the annular brace comprises a wireform that is bent to provide the first and second top and bottom wings. Optionally, the wireform is cut or stamped from a sheet of an elastically deformable biocompatible material.

In an embodiment of the invention an annular brace is mounted to the annulus of a cardiac valve of a patient at a region of each commissure of the valve to treat compromised performance of the valve. Leaflet restraining struts may be mounted to the braces on the atrial side of the valve to constrain motion of the valve leaflets and improve performance of the valve. In an embodiment of the invention the valve may be the mitral or tricuspid valve and the restraining struts are mounted to the atrial side of the valve to prevent prolapse of the leafs into the left or right atrium respectively.

There is therefore provided in accordance with an embodiment of the invention, a brace for mounting to an annulus of a cardiac valve, the brace comprising: first and second bottom gripping wings for gripping the annulus; first and second top gripping wings for gripping the annulus; and a support bridge that connects the top wings to the bottom wings; wherein the brace is deformable from a delivery configuration to a deployed configuration and in the delivery configuration the top wings are oriented substantially back to back along an axis and the bottom wings are oriented substantially back to back along the same axis, and in the deployed configuration the first top and bottom gripping wings face each other to grip the annulus between them and the second top and bottom gripping wings face each other to grip the annulus between them.

In an embodiment of the invention, the first top and first bottom gripping wings are integral parts of a same first strip of material separated by a bridge portion of the first strip. Optionally, the second top and second bottom gripping wings are integral parts of a same second strip of material separated by a bridge portion of the second strip.

In an embodiment of the invention, the first top and second top gripping wings are integral parts of a same first strip of material separated by a bridge portion of the first strip. Optionally, the first bottom and second bottom gripping wings are integral parts of a same second strip of material separated by a bridge portion of the second strip.

In an embodiment of the invention, the first and second strips of material are separate strips that are joined by connecting the bridge portion of the first strip to the bridge portion of the second strip to form the bridge.

In an embodiment of the invention, the first and second strips of material are integral parts of a same flat piece of material that is bent in a region of the piece of material connecting the bridging regions of the first and second strips to form the bridge.

The brace may comprise at least one anchor tooth on at least one or more of the gripping wings that penetrates into the annulus when the brace is mounted to the annulus.

The first top gripping wing may comprise a stabilizer tooth that faces the first bottom gripping wing to grip the annulus between the stabilizer tooth and first bottom gripping wing prior to completion of mounting the brace to the annulus.

In an embodiment of the invention, the brace comprises a wireform having first and second wire-loops connected by the support bridge. Optionally, the support bridge comprises at least one wire segment.

In an embodiment of the invention, the first top and first bottom gripping wings are wireform gripping wings comprised in the first wire-loop.

In an embodiment of the invention, the second top and second bottom gripping wings are wireform gripping wings that are comprised in the second wire-loop.

In an embodiment of the invention, the first and second top gripping wings are wireform gripping wings comprised in the first wire-loop. In an embodiment of the invention, the first and second bottom gripping wings are wireform gripping wings comprised in the second wire-loop.

In an embodiment of the invention, the brace is formed from a shape memory material, and in the delivery configuration the material is in a martensite state and in the deployed configuration the material is in an austenite state.

There is further provided in accordance with an embodiment of the invention apparatus for treating prolapse of a leaflet of a cardiac valve comprising an annulus that supports at least two leaflets that meet at least two commissures, the apparatus comprising: a first brace according to any of the preceding claims configured to be mounted to the annulus in a region of a first commissure of the at least two commissures; a second brace according to any of the preceding claims configured to be mounted to the annulus in a region of a second commissure of the at least two commissures; and at least one restraining strut mountable to the first and second braces after the braces are mounted to the annulus.

In the discussion, unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the description and claims is considered to be the inclusive "or" rather than the exclusive or, and indicates at least one of, or any combination of items it conjoins.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical features that appear in more than one figure are generally labeled with a same label in all the figures in which they appear. A label labeling an icon representing a given feature of an embodiment of the invention in a figure may be used to reference the given feature. Dimensions of features shown in the figures are chosen for convenience and clarity of presentation and are not necessarily shown to scale.

DETAILED DESCRIPTION

Figure 1:
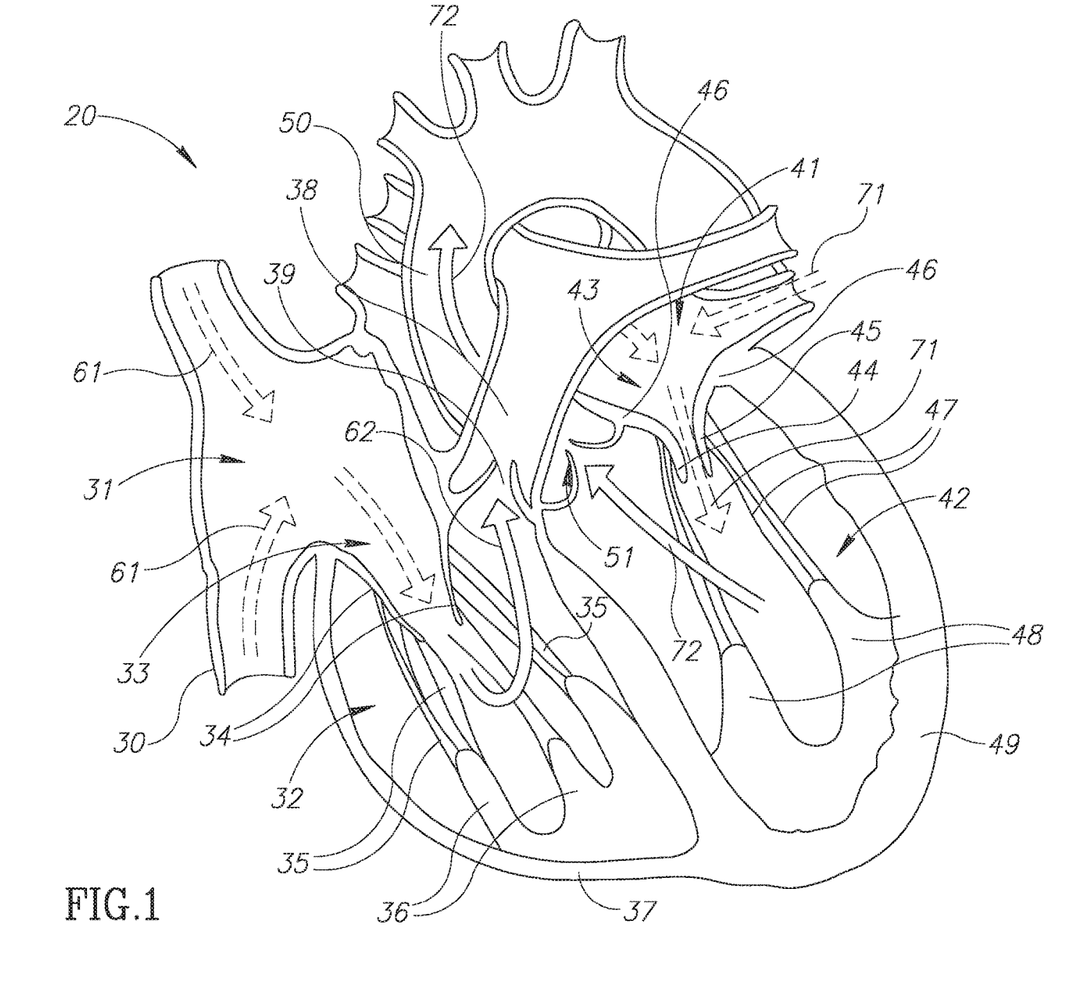
FIG. 1 schematically shows a cross section of a human heart that displays the heart chambers and cardiac valves.

FIG. 1 shows a schematic, stylized cross section of a human heart 20 having a right atrium 31 and a right ventricle 32 that communicate via a tricuspid valve 33 and a left atrium 41 and left ventricle 42 that communicate via a mitral valve 43. Tricuspid valve 33 has three leaflets 34, only two of which are shown in FIG. 1, that are tied by chordae tendineae 35 and papillary muscles 36 to the wall 37 of the right ventricle. Right ventricle 32 communicates with the pulmonary artery 38 via the pulmonary valve 39. Mitral valve 43 has two leaflets, anterior and posterior leaflets 44 (anterior leaflet 44 is in continuity with the wall of the aorta) and 45 respectively that are supported and extend from the mitral annulus 46. Mitral valve leaflets 44 and 45 are respectively tied by chordae tendineae 47 and papillary muscles 48 to the ventricle wall 49. The left ventricle communicates with the aorta 50 via the aortic valve 51.

Deoxygenated blood returning from parts of the body enters right atrium 31 and passes through tricuspid valve 33 to enter right ventricle 32 during diastole when leaflets 34 of the tricuspid valve are separated (as schematically shown in FIG. 1) to open the tricuspid valve and the right ventricle is relaxed. Flow of deoxygenated blood into the right atrium via the inferior vena cava 30 and through tricuspid valve 33 into the right ventricle is schematically indicated by dashed line block arrows 61. During systole right ventricle 32 contracts to pump the deoxygenated blood through pulmonary valve 39 and into pulmonary artery 38 for delivery to the lungs. During systole leaflets 34 of tricuspid valve 33 coapt and the tricuspid valve 33 closes to prevent deoxygenated blood pumped by the right ventricle from regurgitating into the right atrium. Flow of deoxygenated blood pumped by right ventricle 32 into pulmonary artery 38 is schematically indicated by solid line block arrow 62.

Oxygenated blood from the lungs enters left atrium 41 and passes through mitral valve 43 to enter left ventricle 42 during diastole when leaflets 44 and 45 are separated (as shown in FIG. 1) to open the mitral valve and the left ventricle is relaxed. Flow of oxygenated blood into the left atrium and through mitral valve 43 into the left ventricle is schematically indicated by dashed block arrows 71. During systole left ventricle 42 contracts to pump the oxygenated blood through the aortic valve 51 and into the aorta 50 for delivery to the body. During systole leaflets 44 and 45 coapt to close mitral valve 43 and prevent oxygenated blood pumped by the left ventricle from regurgitating into the left atrium.

Valves 33, 39, 43, and 51 operate to direct flow of blood in the heart and out from the heart and their proper and efficient function are required to maintain a person's health and quality of life. Various different disease processes may result in damage to a heart valve and compromise valve functioning. For example, functioning of the mitral valve may be compromised by various degrees of stenosis, calcification, distortion of the mitral valve annulus, torn chordae tendineae, and faulty left ventricle functioning. Valve dysfunction and concomitant regurgitation may become so severe as to warrant surgical intervention to provide a person with an acceptable state of health and quality of life.

Figure 2A:
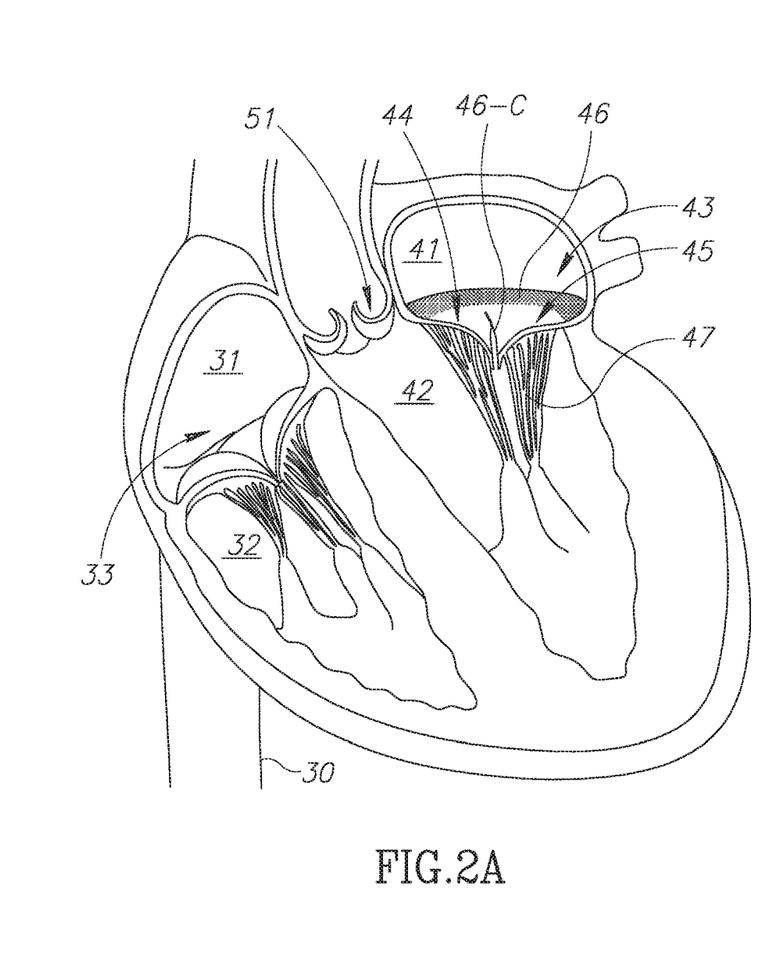
FIG. 2A schematically shows a cutaway perspective view of a human heart that provides a perception of the three dimensional structure of the mitral and tricuspid valves of the heart.
Figure 2B:
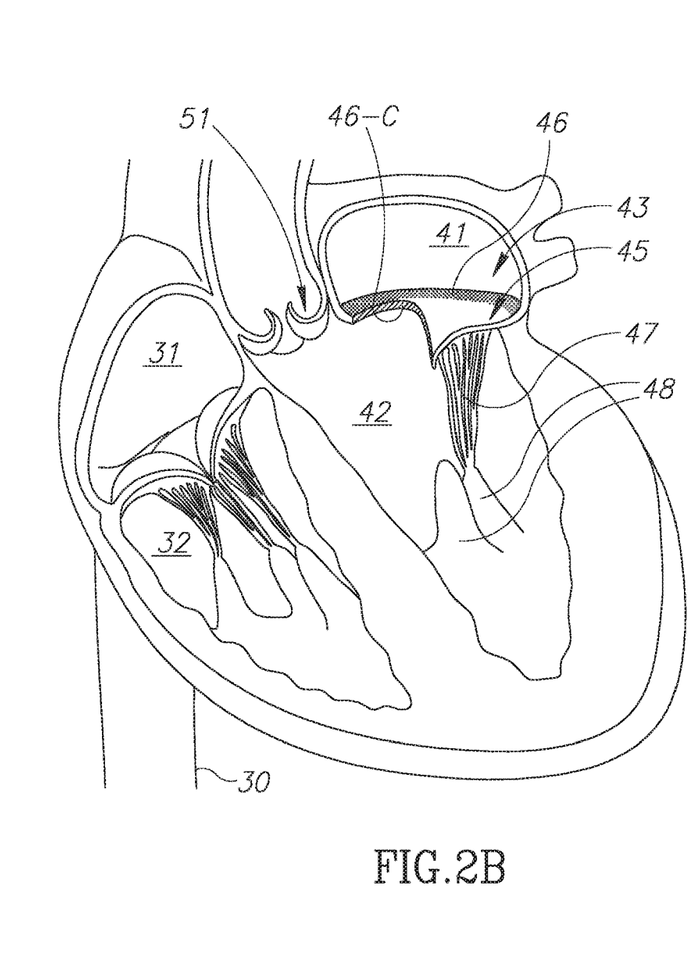
FIG. 2B schematically shows the cutaway perspective view of a human heart similar to that shown in FIG. 2A with the anterior leaflet of the mitral valve cutaway for convenience of presentation.

FIG. 2A schematically shows a cutaway perspective view of a human heart 20 that provides a perception of the three dimensional structure of mitral valve 43 and tricuspid valve 33. In the figure, a portion of annulus 46 of mitral valve 43 that supports mitral valve anterior and posterior leaflets 44 and 45 is shown shaded, and a region of a commissure 46-C at which the leaflets come together is indicated. For convenience of presentation and the discussion that follows, FIG. 2B schematically shows heart 20 in which anterior leaflet 44 shown in FIG. 2A is cutaway substantially to annulus 46, and chordae tendineae 47 that connect the anterior leaflet to papillary muscles 48 are removed.

Figure 3:
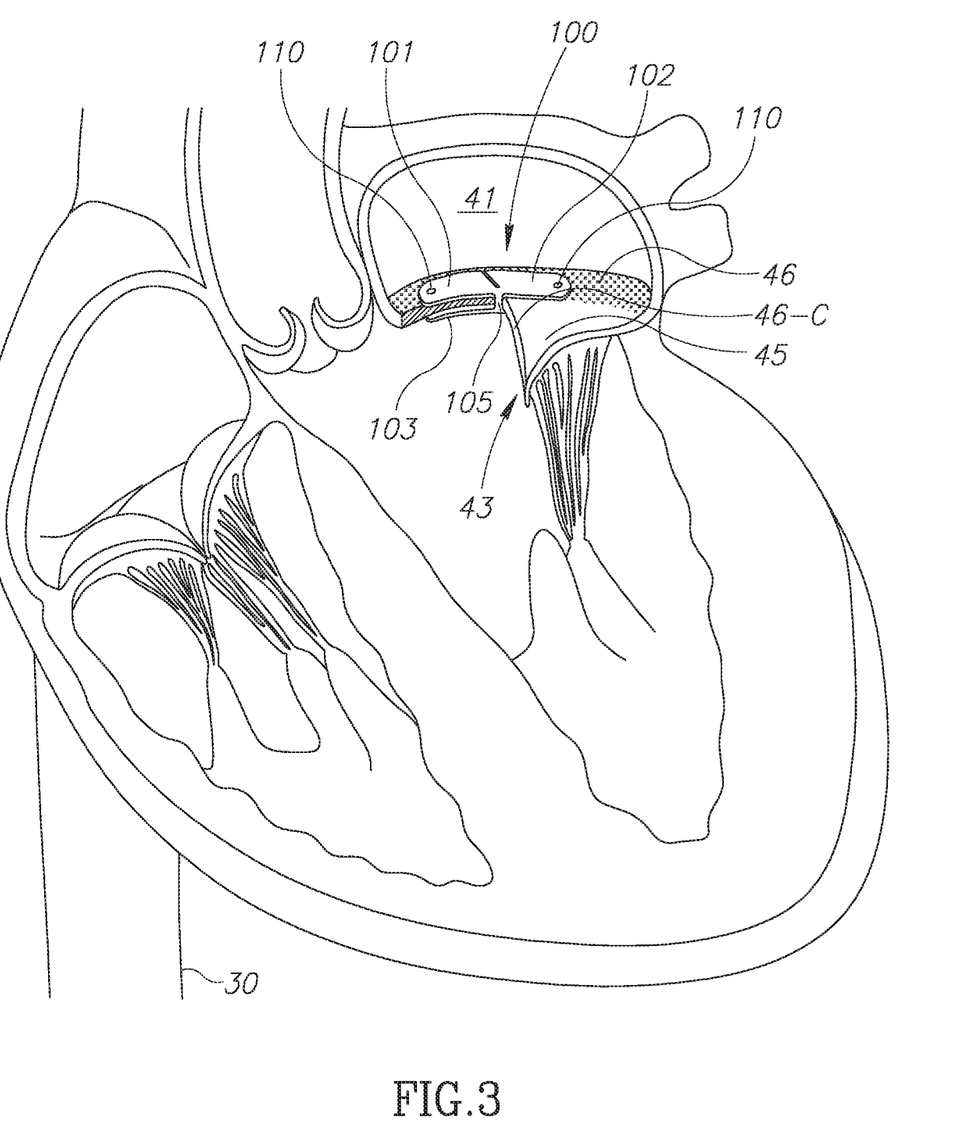
FIG. 3 schematically shows an annular brace mounted to the annulus of the mitral valve shown in FIG. 2B, in accordance with an embodiment of the invention.

FIG. 3 schematically shows an annular brace 100 mounted to annulus 46 in the region of commissure 46-C in accordance with an embodiment of the invention. Annular brace 100 comprises first and second top gripping wings 101 and 102 and first and second bottom gripping wings 103 and 104. In the perspective of FIG. 3 bottom gripping wing 104 is hidden by posterior leaflet 45 and is not shown. Top gripping wings 101 and 102 are joined to bottom gripping wings 103 and 104 by a bridge 105. Optionally, top gripping wings 101 and 102 are formed having mounting holes 110 for mounting apparatus to annular brace 100 that a medical practitioner may determine to be advantageous for ameliorating a mitral valve dysfunction.

Figures 4A, 4B:
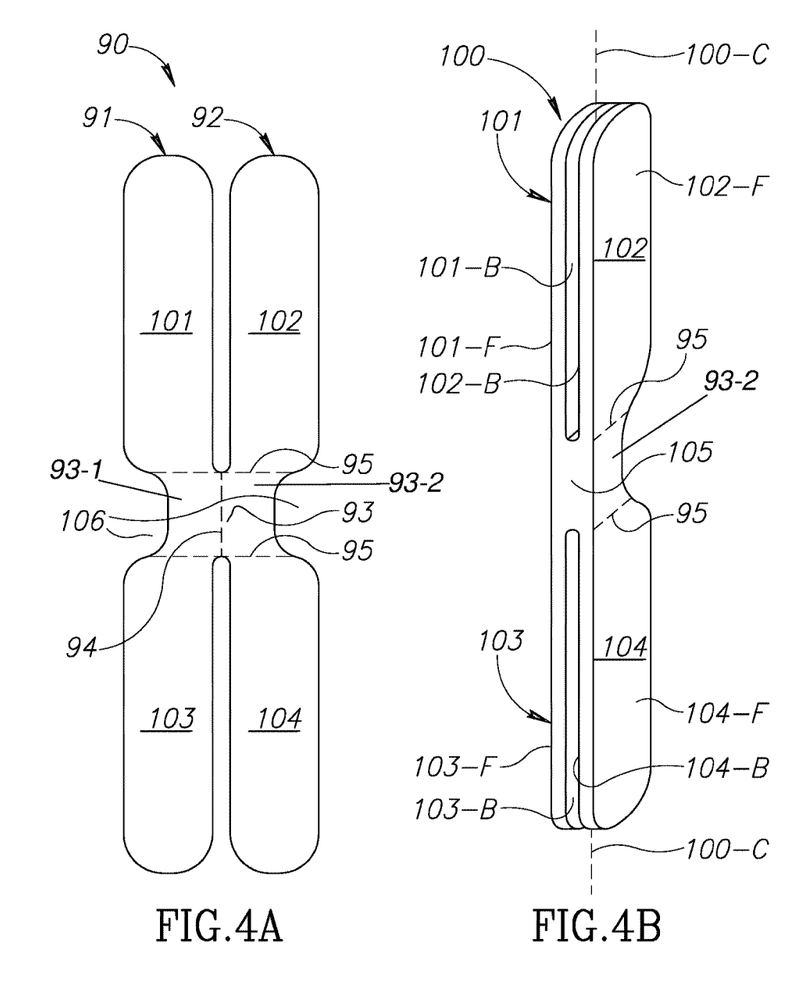
FIGS. 4A-4C schematically illustrate construction of the annular brace shown deployed in FIG. 3, in accordance with an embodiment of the invention.
Figure 4C:
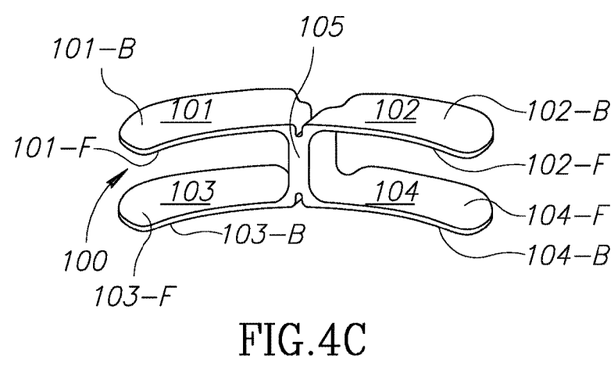

FIGS. 4A-4H schematically illustrate construction and stages in a deployment of annular brace 100 shown in FIG. 3, in accordance with an embodiment of the invention. Brace 100 is optionally formed from a planar die-shape 90, schematically shown in FIG. 4A. The die-shape optionally comprises a gripping strip 91 having top and bottom gripping wings 101 and 103 respectively connected by a bridging portion 93-1, and a gripping strip 92 having top and bottom gripping wings 102 and 104 respectively that are connected by a bridging portion 93-2. A bridging region 93 connects gripping strips 91 and 92. Optionally, die-shape 90 is "scalloped" to produce recesses 106 in which annulus 46 seats when brace 100 is fully deployed as shown in FIG. 3. A dashed line 94 on die-shape 90 indicates a fold line along which bridging region 93 is folded to form bridge 105 (FIG. 3). Folding bridging region 93 along fold line 94 produces annular brace 100 in the brace's delivery configuration as schematically shown in FIG. 4B. Dashed lines 95 shown in FIGS. 4A and 4B indicate bend lines along which gripping wings 101-104 bend to deform brace 100 from the delivery configuration of the brace to the deployed configuration of the brace in which the brace grips annulus 46, as shown in FIG. 3. FIG. 4C shows annular brace 100 as it appears in the deployed configuration, without annulus 46.

Figure 4D:
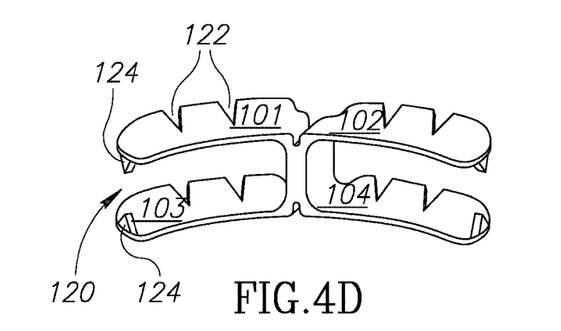
FIGS. 4D and 4E schematically show variations of annular braces similar to the annular brace shown in FIGS. 3 and 4A-4C, in accordance with an embodiment of the invention.
Figure 4E:
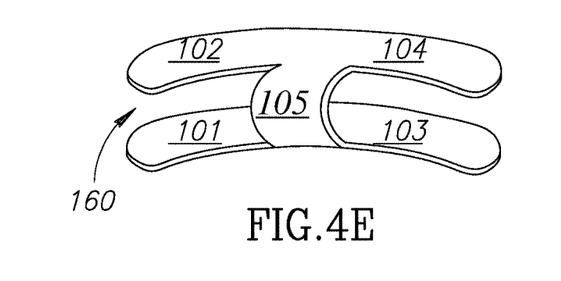

It is noted, as shown in FIGS. 3 and 4C, that in the deployed state, gripping wings 101-104 not only bend along bend lines 95 but also optionally deform to conform to a curvature of annulus 46 at the location of commissure 46-C at which the brace is deployed. In an embodiment of the invention, to enable sufficient curvature of top and bottom gripping wings 101-104 to conform to curvature of a cardiac valve annulus, such as annulus 46 of mitral valve 43 or an annulus of a tricuspid valve, to which an annular brace, similar to annular brace 100, is mounted, the gripping wings may be slotted. Optionally, to facilitate anchoring brace 100 to the cardiac valve annulus, a gripping wing of the brace is formed having an anchor tooth that bites into the annulus when the gripping wing is deployed. In an embodiment of the invention, each wing of the annular brace is fitted, optionally at an end of the gripping wing, with at least one anchor tooth. By way of example FIG. 4D schematically shows an annular brace 120 similar to annular brace 100, in which gripping wings 101-104 are formed having slots 122 that facilitate curving of the gripping wings to conform to curvature of a cardiac valve annulus. Each wing 101-104 comprises an anchoring tooth 124 at an end of the wing.

Die-shape 90 (FIG. 4A) may be produced by way of example, by sintering, molding, or by cutting or stamping, from a sheet of a suitable elastically deformable material. Optionally, the material is a shape memory material which may be a shape memory alloy, such as nitinol, or a shape memory polymer. In an embodiment of the invention, the shape memory material is in a martensite state when brace 100 is in the delivery configuration and is in an austenite state when the brace deforms to the deployed configuration, which is a configuration the shape memory material is conditioned to remember. Any of various methods known in the art may be used to condition brace 100 to remember the deployed configuration. It is noted that a die-shape similar to die-shape 90 may be folded and conditioned to provide an annular brace 160 schematically shown in FIG. 4E that is similar to annular braces 100 and 120, but in which top gripping wings are gripping wings 102 and 104 connected by a bridging region 93-2 and bottom gripping wings are gripping wings 101 and 103 connected by a bridging region 93-1. Top gripping wings 102 and 104 are connected to bottom gripping wings 101 and 103 by a support bridle 105.

Figure 4F:
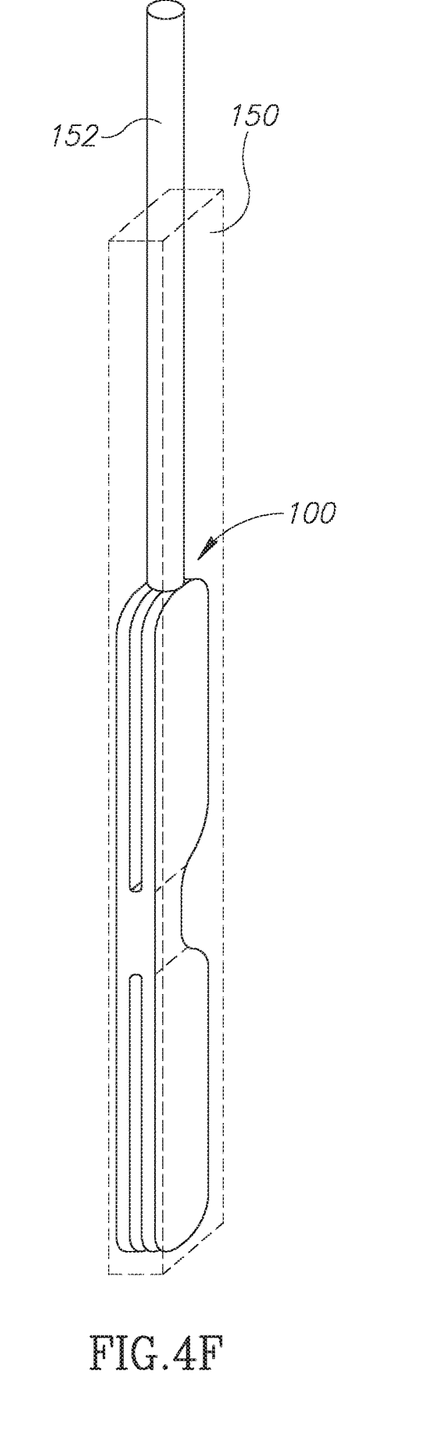
FIGS. 4F-4H schematically show stages in deployment of the brace shown in FIG. 3, in accordance with an embodiment of the invention.
Figure 4G:
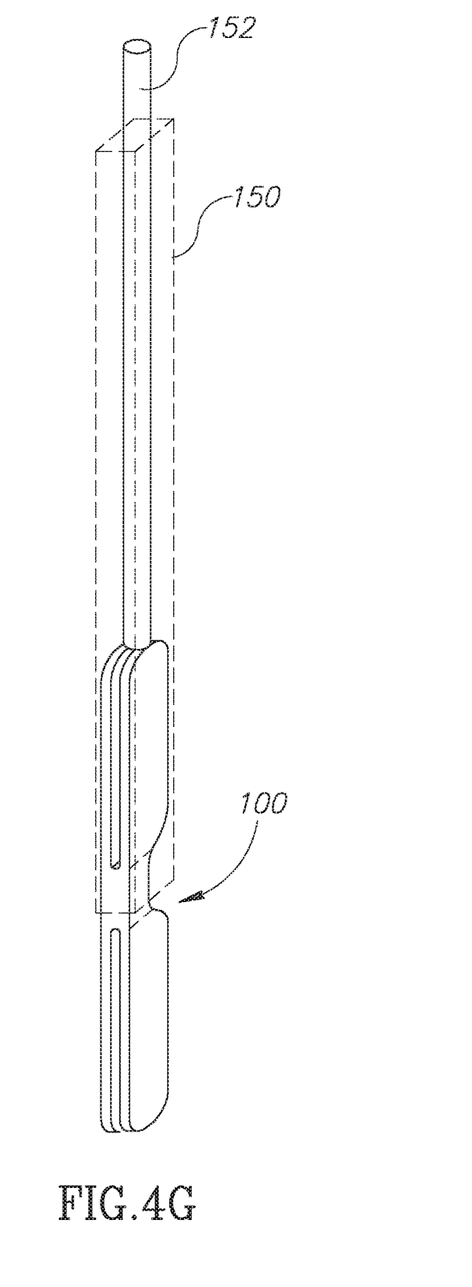
Figures 4H, 4I:
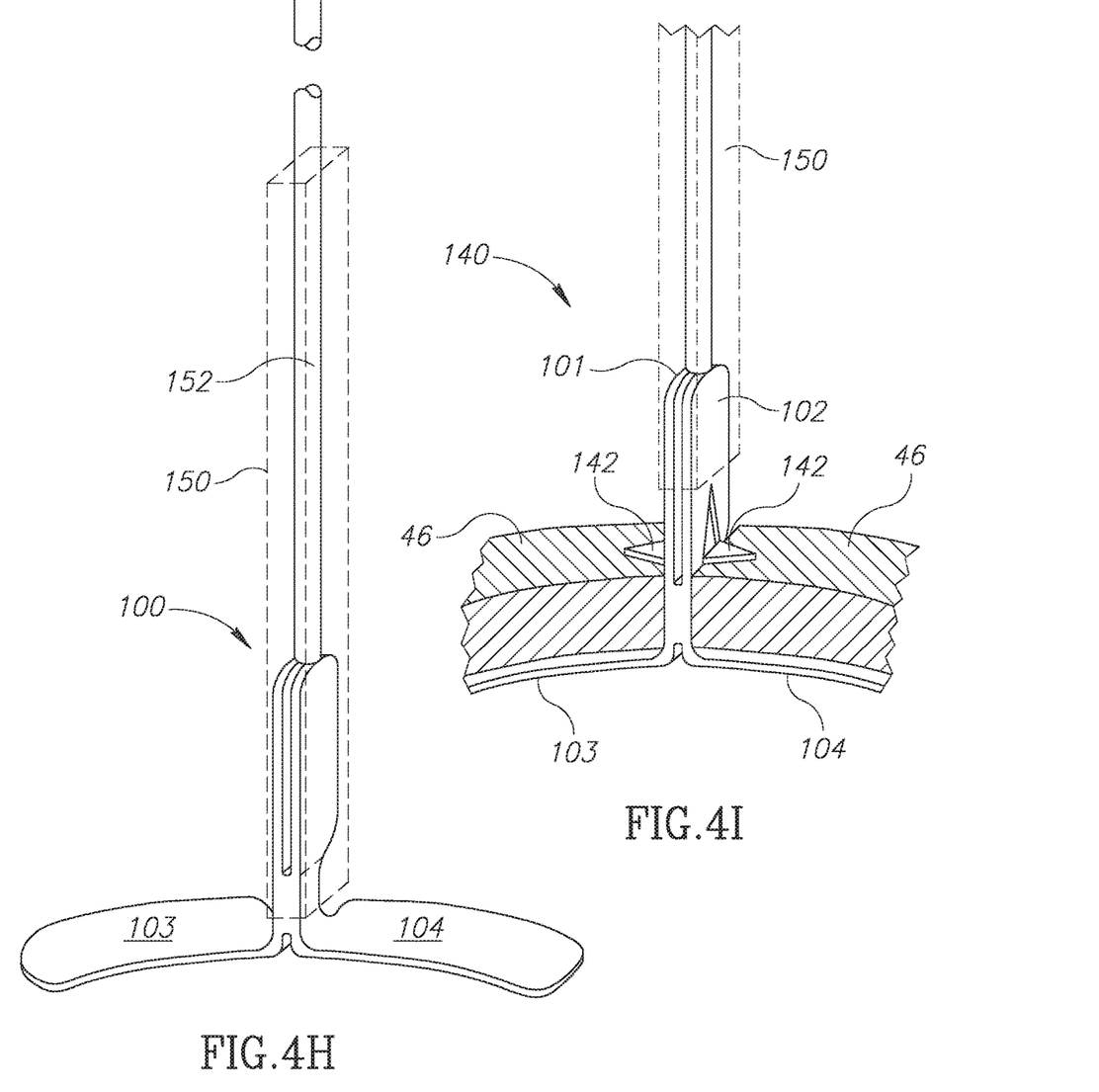
FIG. 4I schematically shows an annular brace having stabilizer teeth that function to facilitate stabilization of deployment of an annular brace during deployment, in accordance with an embodiment of the invention.

FIGS. 4F-4I schematically show stages in the delivery of brace 100 to mitral valve 43, in accordance with an embodiment of the invention. In FIG. 4F brace 100 is housed in a deployment catheter 150 schematically indicated in dashed lines. Optionally deployment catheter 150 has a rectangular or square cross section so that the catheter constrains brace 100 to the brace's delivery configuration as long as the brace is confined by the catheter. Optionally, deployment catheter 150 comprises a push rod 152 that is controllable to push brace 100 out from deployment catheter 150 and deploy the brace at mitral valve 43. FIG. 4G schematically shows annular brace 100 after push rod 152 has partially pushed the brace out of deployment catheter 150 to release bottom gripping wings 103 and 104 from the deployment catheter. Upon being pushed out from deployment catheter 150, and released from confinement by the deployment catheter, bottom gripping wings 103 and 104 bend from bridge 105 away from each other to their deployed orientation as schematically shown in FIG. 4H. Upon push rod 152 pushing annular brace 100 completely out of deployment catheter 150, top gripping wings 101 and 102 bend to their deployed state as shown in FIG. 4C and grip annulus 46 as shown in FIG. 3.

FIGS. 4F-4I show delivery catheter 150 fitting snugly to brace 100 and constraining the brace to a delivery configuration in which the brace appears to fit snugly in a rectangular volume. However, in an embodiment of the invention, delivery catheter 150 may have a sufficiently large cross section to allow a brace, similar to brace 100 to be delivered in a delivery configuration that is partially deformed from the delivery configuration shown in FIGS. 4B and 4F to the deployed configuration shown in FIG. 4C.

By way of a numerical example, die shape 90 may have a thickness between about 0.5 mm to about 3 mm, wings 101-104 may lengths between about 5 mm to about 20 mm and widths between about 2 mm and about 5 mm. Delivery catheter may have an internal diameter up to about 7.5 mm.

In some embodiments of the invention an annular brace similar to annular brace 100 may have stabilizer teeth that deploy from top gripping wings as the annular brace is pushed out of deployment catheter 150 after bottom gripping wings 103 and 104 are deployed and a portion, but not all, of top gripping wings 101 and 102 are released from the deployment catheter. The stabilizer teeth aid in maintaining position of the annular brace during deployment of the brace. FIG. 4I schematically shows an annular brace 140 having stabilizer teeth 142 deployed on an upper surface of annulus 46 after bottom gripping wings 103 and 104 are deployed and top gripping wings 101 and 102 are partially extended from deployment catheter 150.

Figure 5A:
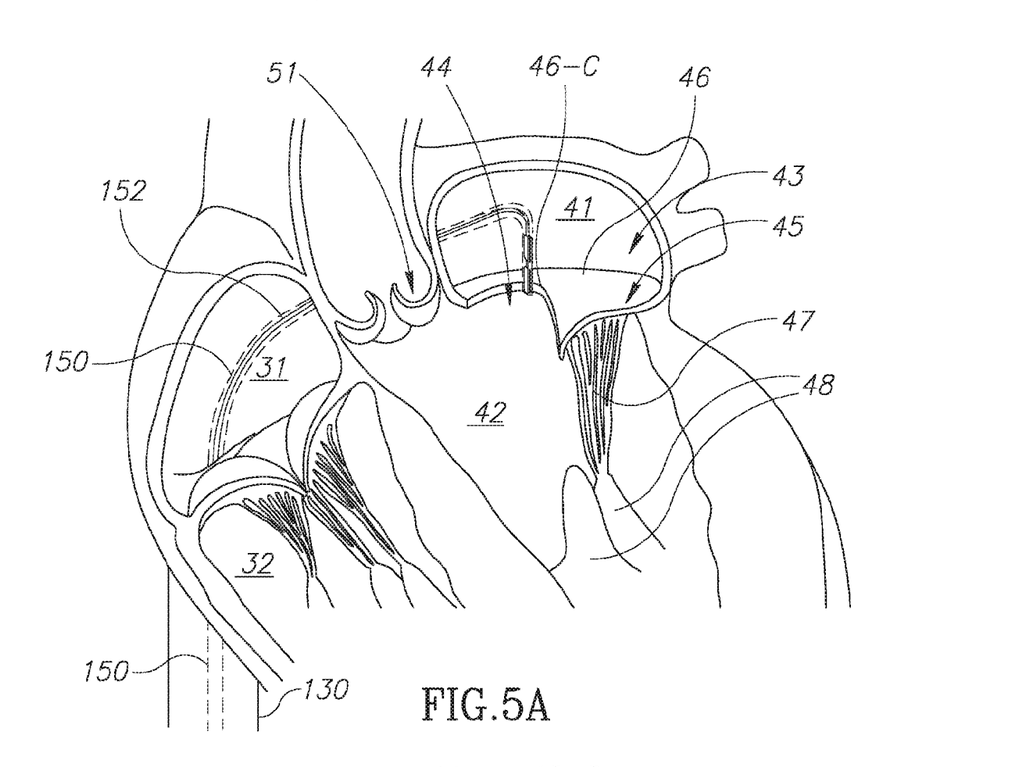
FIGS. 5A-5D schematically illustrate a transseptal deployment of the annular brace shown in FIGS. 3 and 4A-4G, in accordance with an embodiment of the invention.
Figure 5B:
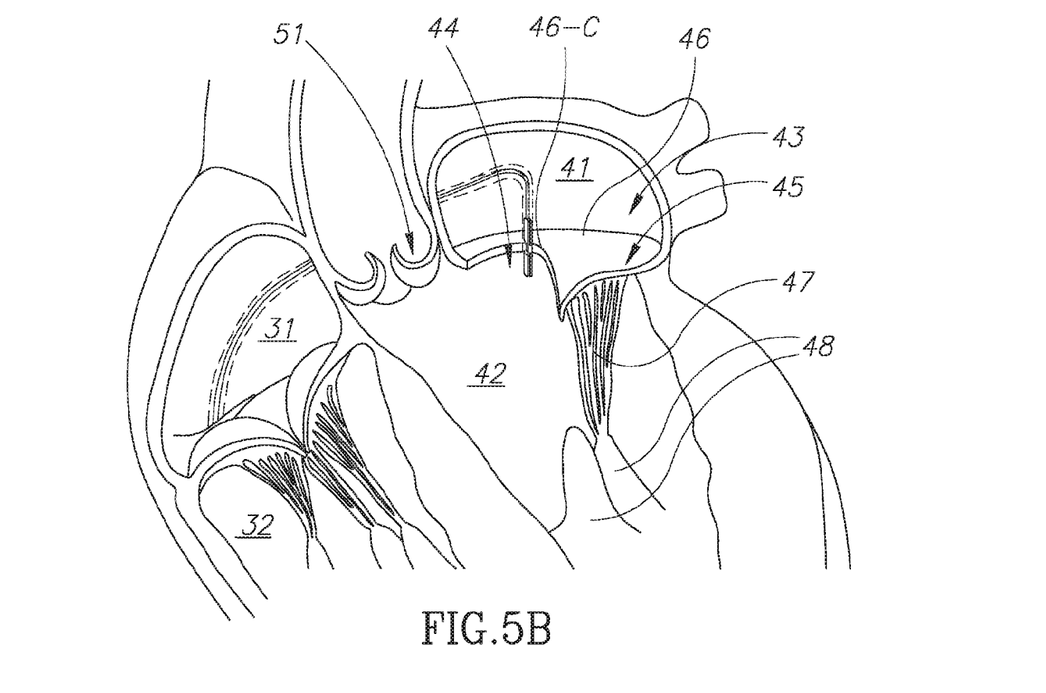
Figure 5C:
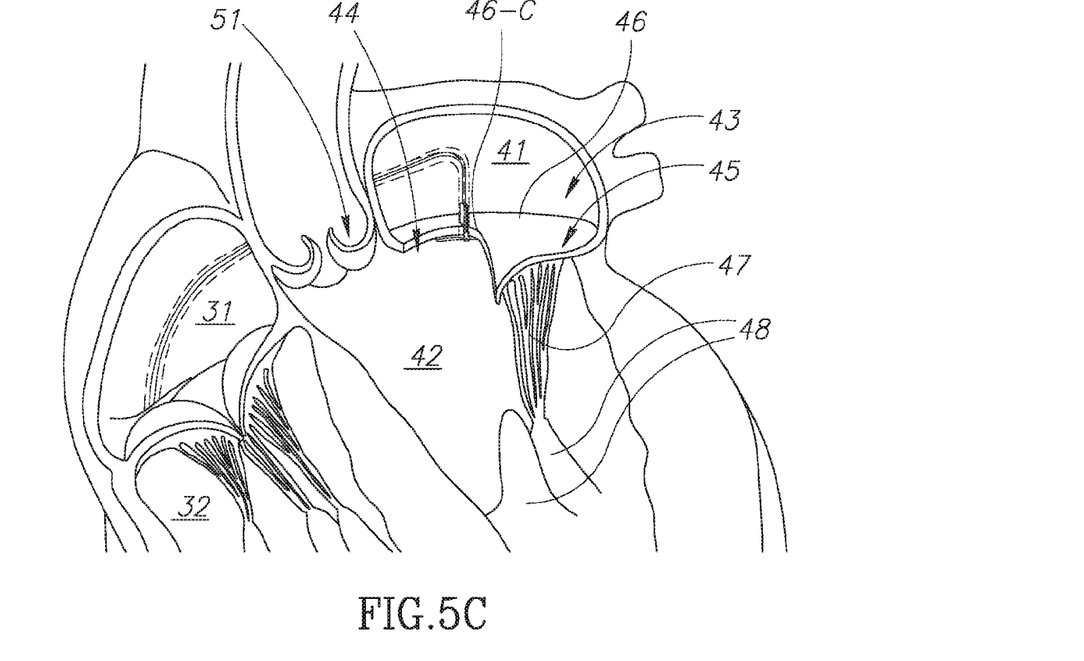
Figure 5D:
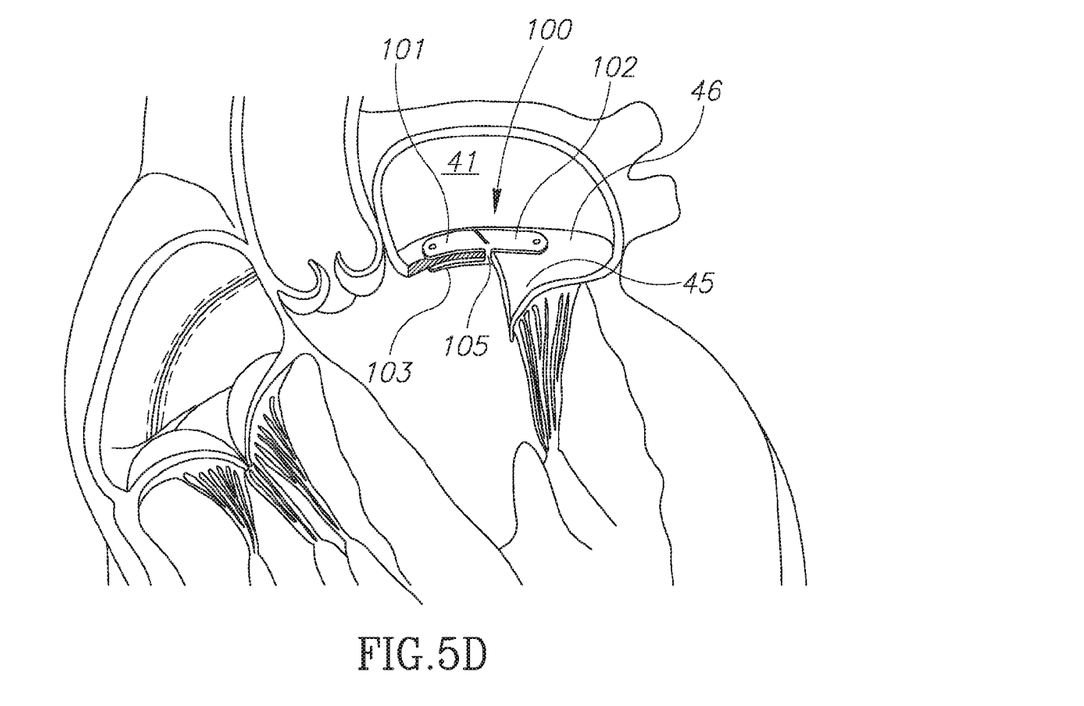

FIGS. 5A-5D schematically show a transseptal procedure for deploying annular brace 100 at mitral valve 43, in accordance with an embodiment of the invention. FIG. 5A schematically shows deployment catheter 150 after the deployment catheter has been threaded into right atrium 31 via the inferior vena cava 30 (FIGS. 1-2B) and been delivered through a puncture in the atrial septum (not shown) into the left atrium. In the left atrium, deployment catheter 150 has been controlled to position annular brace 100 housed in the catheter for mounting to annulus 46. In FIG. 5A annular brace 100 is housed in catheter 150 as shown in FIG. 4F. In FIG. 5B push rod 152 has been controlled to push annular brace 100 out from deployment catheter 150 so that bottom gripping wings 103 and 104 protrude between anterior and posterior leaflets 44 and 45 (FIGS. 1 and 2A) in a region of commissure 46-C to below the leaflets, and recess 106 cups the annulus. The position of bottom gripping wings 103 and 104 in FIG. 5B relative to deployment catheter 150 is similar to that shown in FIG. 4G. Having been released from deployment catheter 150, gripping wings 103 and 104 bend apart to their respective deployment locations under annulus 46 to the left and right respectively of commissure 46-C as schematically shown in FIG. 5C. In FIG. 5D push road 152 has pushed annular brace 100 completely out of deployment catheter 150, top gripping wings 101 and 102 have bent to their deployed configuration opposite gripping wings 103 and 104 respectively and deployment catheter 150 has been removed from left atrium 41. Top and bottom gripping wings 101 and 103 sandwich, grip, and anchor to a region of annulus 46 between them and top to the left of commissure 46-C and bottom gripping wings 102 and 104 sandwich, grip, and anchor to a region of annulus 46 between them to the right of commissure 46-C. Annular brace 100 is fully deployed and mounted to annulus 46 at commissure 46-C.

Figure 6:
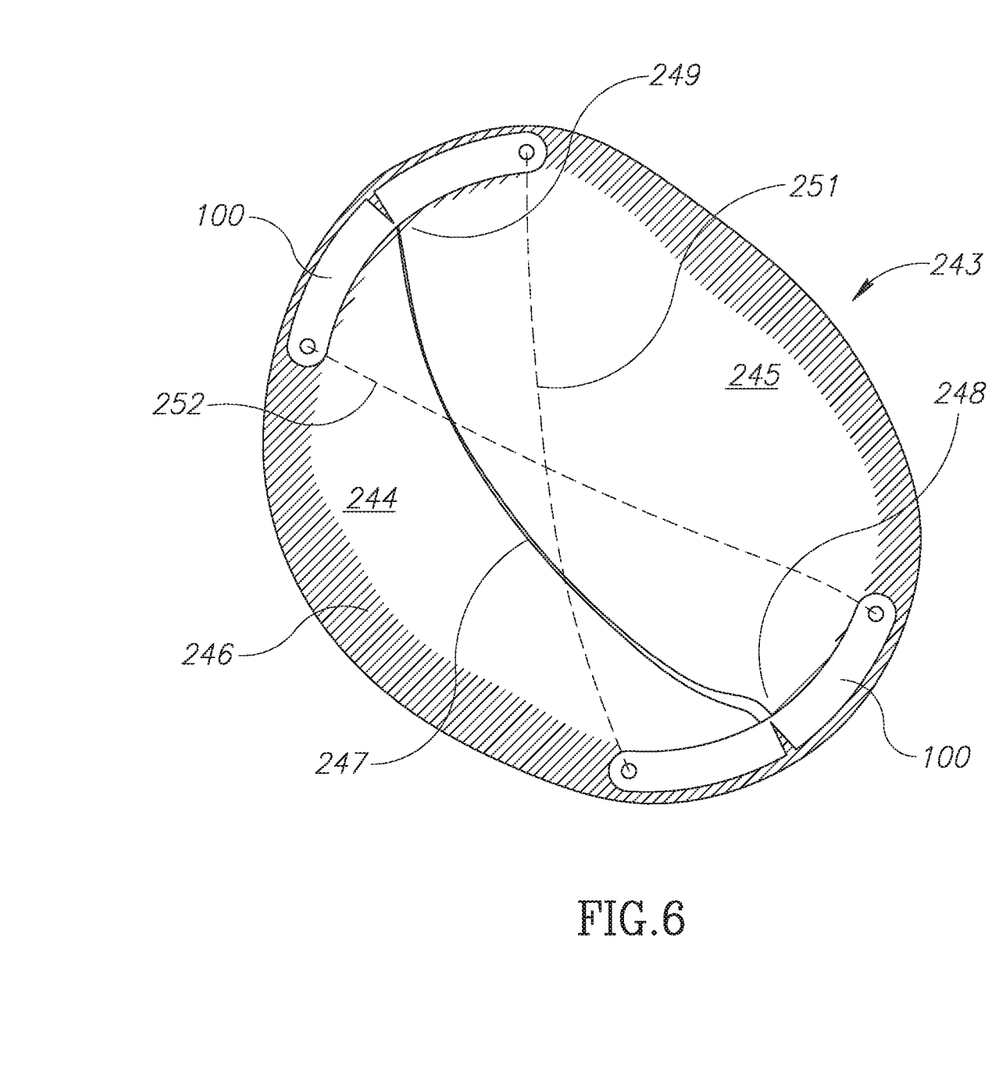
FIG. 6 schematically shows a view from the atrial side of a mitral valve having an annular brace mounted at each commissure of the valve and leaflet restraining struts mounted to the braces, in accordance with an embodiment of the invention.

FIG. 6 schematically shows a view from the atrial side of a mitral valve 243 comprising leaflets 244 and 245 that are supported by an annulus 246 shown shaded and operate to coapt along a seam 247 that extends between commissures 248 and 249. Function of mitral valve 243 is assumed to be compromised by prolapse of leaflets 244 and 245 into the atrium. To alleviate prolapse, in accordance with an embodiment of the invention, an annular brace 100 is mounted to annulus 246 at each commissure 248 and 249 of the valve, and leaflet restraining struts 251 and 252 are mounted to braces 100 to restrain motion of the leaflets into the atrium.

Figures 7A, 7B:
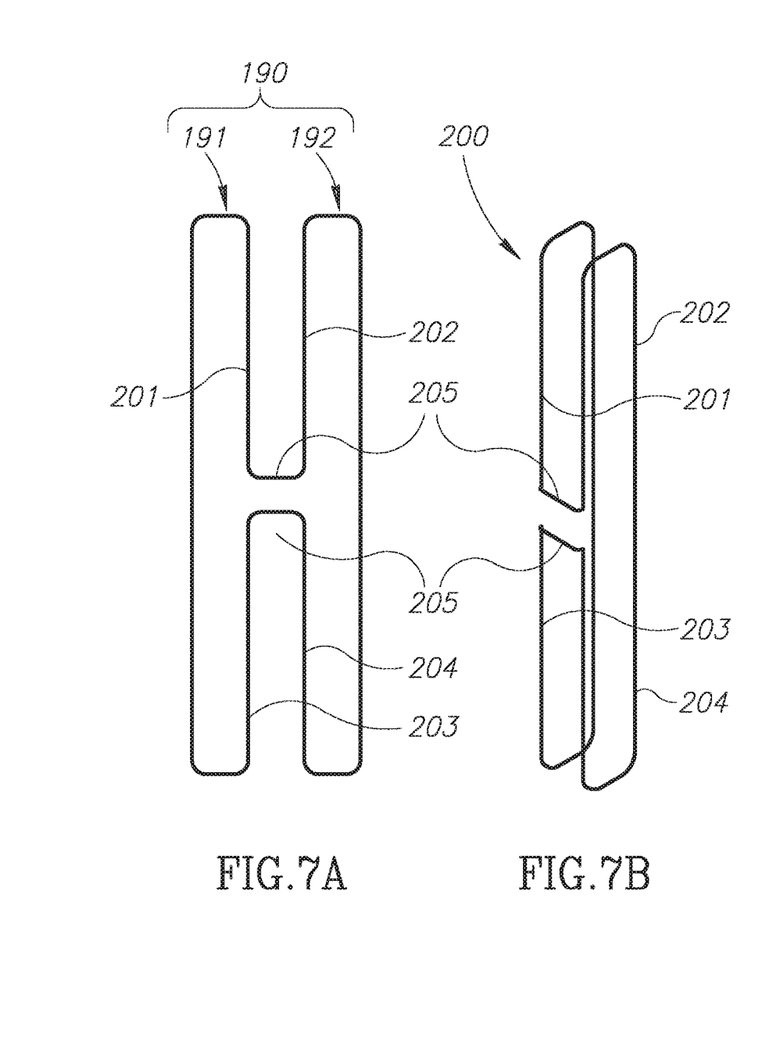
FIGS. 7A-7D schematically show a wireframe annular brace, in accordance with an embodiment of the invention.
Figure 7C:
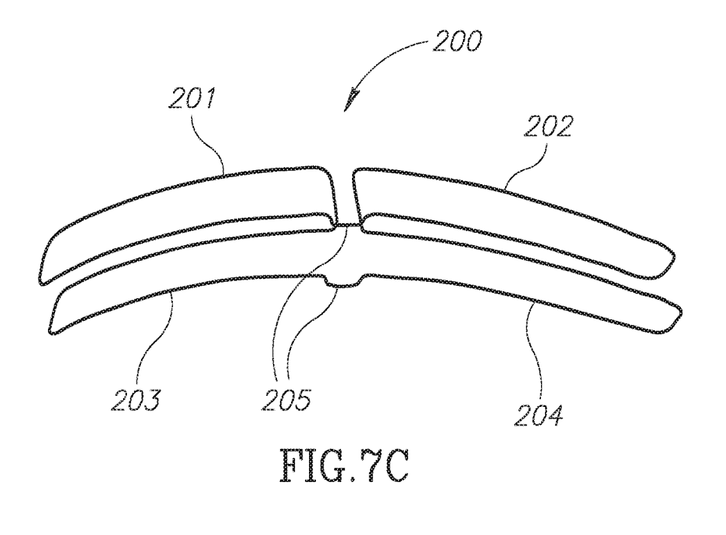

FIGS. 7A-7C schematically illustrate construction of an annular wireframe brace 200, in accordance with an embodiment of the invention.

Figure 7D:
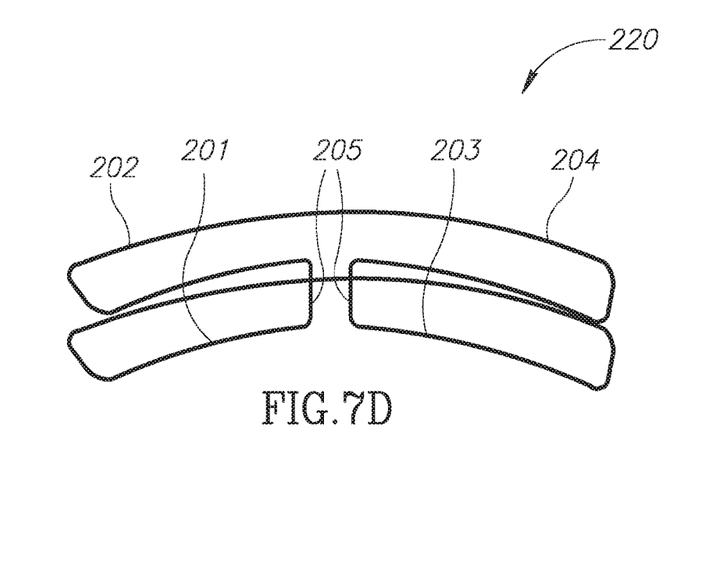

FIG. 7A schematically shows a wireform "blank" 190 after the wireform has optionally been cut from a sheet of a suitable deformable biocompatible material or formed from a wire of such a material, in accordance with an embodiment of the invention. Wireform blank 190 optionally comprises two bridge wires 205 that connect wire-loops 191 and 192. Wire-loop 191 comprises top and bottom wire gripping wings 201 and 203 respectively. Wire-loop 192 comprises top and bottom wire gripping wings 202 and 204 respectively. Bending wire-loops 191 and 192 in regions where the wire-loops meet bridge wires 205 as schematically shown in FIG. 7B produces wireframe annular brace 200 in a delivery configuration. FIG. 7C schematically shows wireframe annular brace 200 in a deployed configuration. It is noted that wireform blank 190 may be folded and conditioned to provide a wireframe annular brace 220 shown in FIG. 7D in which top wire gripping wings are gripping wings 202 and 204 and bottom gripping wings are gripping wings 201 and 203. Wireform annular brace 220 is shown in a deployed configuration in FIG. 7D.

Similarly, to annular brace 100 an annular wire brace in accordance with an embodiment of the invention may be formed having gripping teeth and stabilizer teeth. And whereas wire-loops 191 and 192 are shown as simple wire loops formed from straight wire sections, wire-loops in accordance with an embodiment of the invention may be formed from wavy wire sections or may comprise a wire mesh.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A brace for mounting to an annulus of a cardiac valve, the brace comprising:
   first and second bottom gripping wings for gripping the annulus;
   first and second top gripping wings for gripping the annulus; and
   a support bridge that connects the top wings to the bottom wings;
   wherein the brace is formed from a shape memory material and the first top and the first bottom gripping wings, or the first and the second top gripping wings, are integral parts of a same first strip of the shape memory material separated by a bridge portion of the first strip and wherein the brace is deformable from a delivery configuration to a deployed configuration and in the delivery configuration the top wings are oriented substantially back to back along an axis and the bottom wings are oriented substantially back to back along the same axis, and in the deployed configuration the brace assumes an H-like shape the first and second top gripping wings are adjacent, extend away from the support bridge in opposite directions to lie along adjacent portions of the annulus the first and second bottom gripping wings are adjacent, extend away from the support bridge in opposite directions to lie along adjacent portions of the annulus, and the first top and bottom gripping wings face each other to grip the annulus between them and the second top and bottom gripping wings face each other to grip the annulus between them.

2. The brace according to claim 1 wherein the first top and first bottom gripping wings are integral parts of the same first strip of material separated by the bridge portion of the first strip.

3. The brace according to claim 2 wherein the second top and second bottom gripping wings are integral parts of a same second strip of material separated by a bridge portion of the second strip.

4. The brace according to claim 1 wherein the first top and second top gripping wings are integral parts of the same first strip of material separated by the bridge portion of the first strip.

5. The brace according to claim 4 wherein the first bottom and second bottom gripping wings are integral parts of a same second strip of material separated by a bridge portion of the second strip.

6. The brace according to claim 3 wherein the first and second strips of material are separate strips that are joined by connecting the bridge portion of the first strip to the bridge portion of the second strip to form the support bridge.

7. The brace according to claim 3 wherein the first and second strips of material are integral parts of a same flat piece of material that is bent in a region of the piece of material connecting the bridging portions of the first and second strips to form the support bridge.

8. The brace according to claim 1 and comprising at least one anchor tooth on at least one or more of the first bottom gripping wing, first top gripping wing, second bottom gripping wing, or second top gripping wing that penetrates into the annulus when the brace is mounted to the annulus.

9. The brace according to claim 1 wherein the first top gripping wing comprises a stabilizer tooth that is deployable to face the first bottom gripping wing and grip the annulus between the stabilizer tooth and first bottom gripping wing independent of deployment of the first top gripping wing.

10. The brace according to claim 1 wherein in the deployed configuration each of the first and second top and first and second bottom gripping wings has external edges that are on opposite sides of the gripping wing and extend from the support bridge along the annulus.

11. The brace according to claim 10 wherein in the deployed configuration each of the external edges on opposite sides of the gripping wing is curved to follow a contour of the annulus.

12. The brace according to claim 11 wherein each of the external edges on opposite sides of the gripping wing has a center of curvature on a same side of the gripping wing.

* * * * *